(12) United States Patent
Isogai et al.

(10) Patent No.: US 7,226,683 B2
(45) Date of Patent: Jun. 5, 2007

(54) PROTON CONDUCTOR AND METHOD OF PRODUCING THE SAME

(75) Inventors: Yuji Isogai, Iruma-gun (JP); Hitoshi Iwadate, Shiki (JP)

(73) Assignee: Honda Motor Co., Ltd., Tokyo (JP)

( * ) Notice: Subject to any disclaimer, the term of this patent is extended or adjusted under 35 U.S.C. 154(b) by 436 days.

(21) Appl. No.: 10/746,789

(22) Filed: Dec. 23, 2003

(65) Prior Publication Data
US 2004/0140433 A1 Jul. 22, 2004

(30) Foreign Application Priority Data
Dec. 27, 2002 (JP) .............................. 2002-380061

(51) Int. Cl.
*H01M 8/10* (2006.01)
*G01N 21/01* (2006.01)
(52) U.S. Cl. ........................ 429/30; 429/33; 250/428
(58) Field of Classification Search ................. 429/30, 429/33; 250/428
See application file for complete search history.

(56) References Cited

U.S. PATENT DOCUMENTS 5,682,261 A    10/1997   Takada et al.

FOREIGN PATENT DOCUMENTS

| JP | 8-249923 | 9/1996 |
|---|---|---|
| JP | 10-069817 | 3/1998 |
| JP | 11-203936 | 7/1999 |
| JP | 2003281933 A | * 10/2003 |

OTHER PUBLICATIONS

C. Fernandez-Lorenzo et al., Sol-gel synthesis of $SiO_2$–$P_2O_5$ glasses, Journal of Non-Crystalline Solids, vol. 176, 1994, pp. 189-199.

* cited by examiner

*Primary Examiner*—Gregg Cantelmo
(74) *Attorney, Agent, or Firm*—Lahive & Cockfield, LLP; Anthony A. Laurentano, Esq.

(57) ABSTRACT

An alcohol solution of a metal alkoxide is mixed with a $H_3PO_4$ mixture solution of water and alcohol to hydrolyze the metal alkoxide and effect crosslinking with $H_3PO_4$. Accordingly, a solid is produced composed of a composite oxide glass (proton conductor) containing constituent elements of P and a metal element originating from the metal alkoxide and having hydroxyl groups at terminals. The metal alkoxide is selected so that the metal alkoxide contains constituent elements of metal elements each of which is designated by a chemical shift within −25 ppm. The chemical shift is a difference between a value at which a peak of orthophosphoric acid appears when a silicon oxide-phosphate glass, which is a composite oxide of phosphorus oxide and silicon oxide, is analyzed by $P^{31}$—MASNMR and a value at which a maximum peak appears when the composite oxide glass is analyzed by $P^{31}$—MASNMR.

5 Claims, 7 Drawing Sheets

PROTON CONDUCTOR AND METHOD OF PRODUCING THE SAME

BACKGROUND OF THE INVENTION

1. Field of the Invention

The present invention relates to a proton conductor and a method of producing the same. In particular, the present invention relates to a proton conductor which exhibits an excellent proton conductivity and which hardly causes hydrolysis, and a method of producing the same.

2. Description of the Related Art

Recently, a proton conductor is used as an electrolyte for a fuel cell. In such a case, all components of the fuel cell can be constructed with solid materials, because the proton conductor is a solid. Therefore, it is possible to obtain a simple structure. Further, it is possible to decrease the frequency of maintenance operation, because no liquid leakage occurs.

The proton conductor, in which the proton conductivity is large, includes glasses obtained by compounding silicon oxide and Brønsted acid as described, for example, in Japanese Laid-Open Patent Publication Nos. 8-249923, 10-69817, and 11-203936. For example, the compound, which is obtained by doping silicon oxide with phosphoric acid as Brønsted acid, is adhered by a binder of any one of a thermoplastic elastomer (Japanese Laid-Open Patent Publication No. 8-249923), a polymer having sulfone group on the side chain (Japanese Laid-Open Patent Publication No. 10-69817), and a sulfonated product of block copolymer composed of conjugated diene unit and aromatic vinyl unit (Japanese Laid-Open Patent Publication No. 11-203936). Accordingly, the proton conductor is obtained.

The glass based on silicon oxide-phosphoric acid (hereinafter referred to as "Si—P-based glass"), which includes phosphoric acid in the SiO$_2$ network structure as described in Japanese Laid-Open Patent Publication Nos. 8-249923, 10-69817, and 11-203936, the glass absorbs moisture or water in the atmospheric air, and it undergoes hydrolysis, resulting in liberation of orthophosphoric acid. C. Fernandez-Lorenzo et al. describes this phenomenon in Journal of Non-Crystalline Solids, Vol. 176, 1994, pp. 189–199 (especially, p. 197, left column, lines 24–28). Therefore, the proton conductivity of the Si—P-based glass may be lowered as the time elapses.

When the Si—P-based glass, which has the network-shaped SiO$_2$ backbone doped with phosphoric acid (P$_2$O$_5$), is used as an electrolyte for a fuel cell, the proton conductivity of the electrolyte may be lowered as the time elapses. In such a situation, it is impossible to obtain predetermined power generation performance.

SUMMARY OF THE INVENTION

A general object of the present invention is to provide a proton conductor which hardly causes hydrolysis but exhibits excellent proton conductivity, and is preferable as, for example, a solid electrolyte for a fuel cell.

According to the present invention, a proton conductor as a composite oxide contains a metal element which is designated or specified by a chemical shift within –25 ppm. The chemical shift is a difference between a value at which a peak of orthophosphoric acid appears when a silicon oxide-phosphate glass, which is a composite oxide of phosphorus oxide and silicon oxide, is analyzed by P$^{31}$—MASNMR and a value at which a maximum peak appears when the composite oxide is analyzed by P$^{31}$-MASNMR. The term "MASNMR" herein means "Magic Angle Spinning Nuclear Magnetic Resonance" which is one of the techniques for measuring and analyzing solid samples by means of the nuclear magnetic resonance.

Preferred examples of the metal element include any one selected from the group consisting of lanthanoid elements, Ti, Zr, Hf, Ta, and Ge. In particular, when the metal element is La as the lanthanoid element, the proton conductivity is satisfactory.

Another object of the present invention is to provide a method of producing a proton conductor, in which it is possible to manufacture a composite oxide as the proton conductor with ease and it is easy to control the composition ratio between phosphorus and the metal element other than phosphorus in the composite oxide.

Still another object of the present invention is to provide a method of producing a proton conductor, in which the structure of a composite oxide is further stabilized.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

The proton conductor and the method of producing the same according to the present invention will be exemplified below by preferred embodiments, which will be explained in detail with reference to the accompanying drawings.

The proton conductor according to the embodiments of the present invention is a composite oxide having a composition formula represented by P$_x$Me$_y$O$_m$H$_n$ provided that Me represents a metal element as described later on. Specifically, the proton conductor is a composite oxide glass having hydroxyl groups (—OH) bonded to terminals of an amorphous composite oxide composed of P and Me as illustrated in a structure shown below.

This structural formula exemplarily shows a form of bonding obtained when Me is a trivalent metal element. However, when Me is, for example, a tetravalent or pentavalent metal element other than the trivalent metal element, the form of bonding changes depending on the valence.

The following metal element is selected as Me. The difference (chemical shift) is within −25 ppm between a value at which a peak of orthophosphoric acid, i.e., $H_3PO_4$ or $PO(OH)_3$ appears when a silicon oxide-phosphate glass is analyzed by $P^{31}$-MASNMR and a value at which a maximum peak appears when the composite oxide glass containing Me is analyzed by $P^{31}$-MASNMR. Metal elements, in which the chemical shift is within −15 ppm, are much preferred.

Also, it is preferable that the composite oxide glasses exhibiting high proton conductivities are obtained with Me.

Preferred examples of such metal element may include lanthanoid elements, Ti, Zr, Hf, Ta, and Ge. In particular, when the metal element is La as a lanthanoid element, it is preferable since excellent proton conductivity is exhibited within a temperature range of 80 to 100° C.

Figure 1:
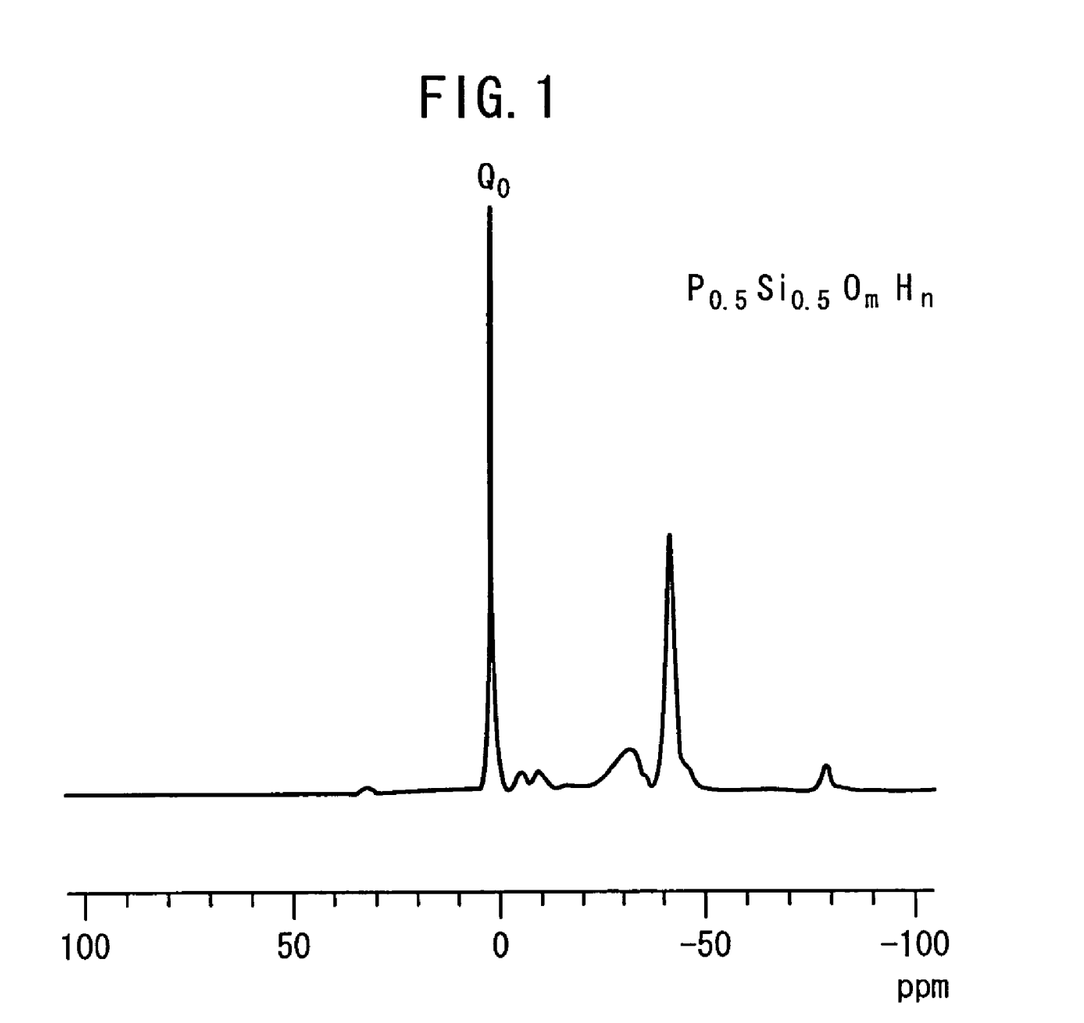
FIG. 1 is a chart of P$^{31}$-MASNMR for a P$_{0.5}$Si$_{0.5}$O$_m$H$_n$ glass.

FIG. 1 shows a chart of $P^{31}$-MASNMR for a silicon oxide-phosphate glass represented by a composition formula of $P_{0.5}Si_{0.5}O_mH_n$. As clearly understood from FIG. 1, as for this glass, a peak $Q_0$ of orthophosphoric acid appears at 0 ppm. This means that orthophosphoric acid is produced as a result of hydrolysis in the glass.

Figure 2:
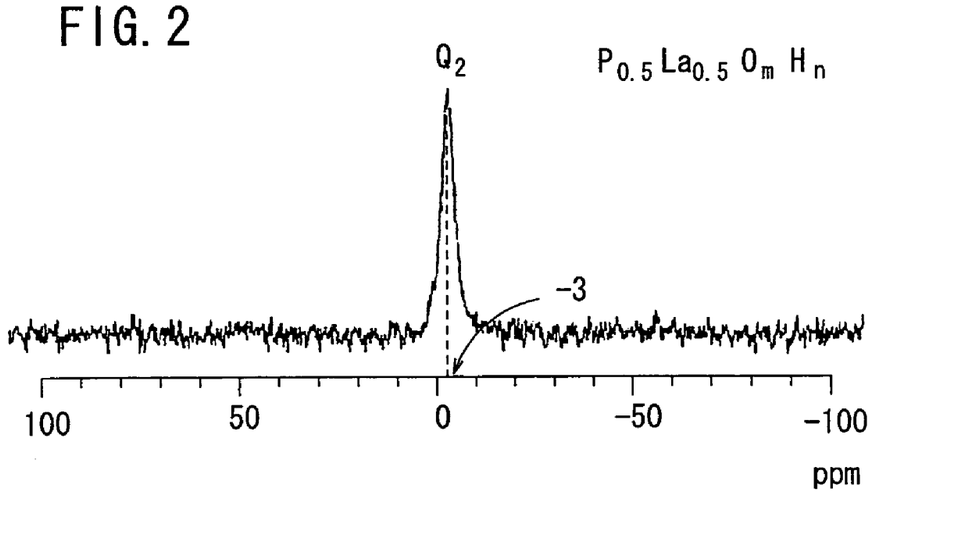
FIG. 2 is a chart of P$^{31}$-MASNMR for a P$_{0.5}$La$_{0.5}$O$_m$H$_n$ composite oxide glass as a proton conductor according to an embodiment of the present invention.

On the other hand, as shown in FIG. 2, a broad peak $Q_2$, which has an apex in the vicinity of −3 ppm, appears in a chart of $P^{31}$—MASNMR for a composite oxide glass of P and La having a composition formula represented by $P_{0.5}La_{0.5}O_mH_n$.

The chemical shift is −3 ppm in this case. According to the fact that the peak $Q_0$ does not appear at 0 ppm in the chart, it is understood that no orthophosphoric acid exists in the glass, in other words, no hydrolysis is caused in the glass.

Figure 3:
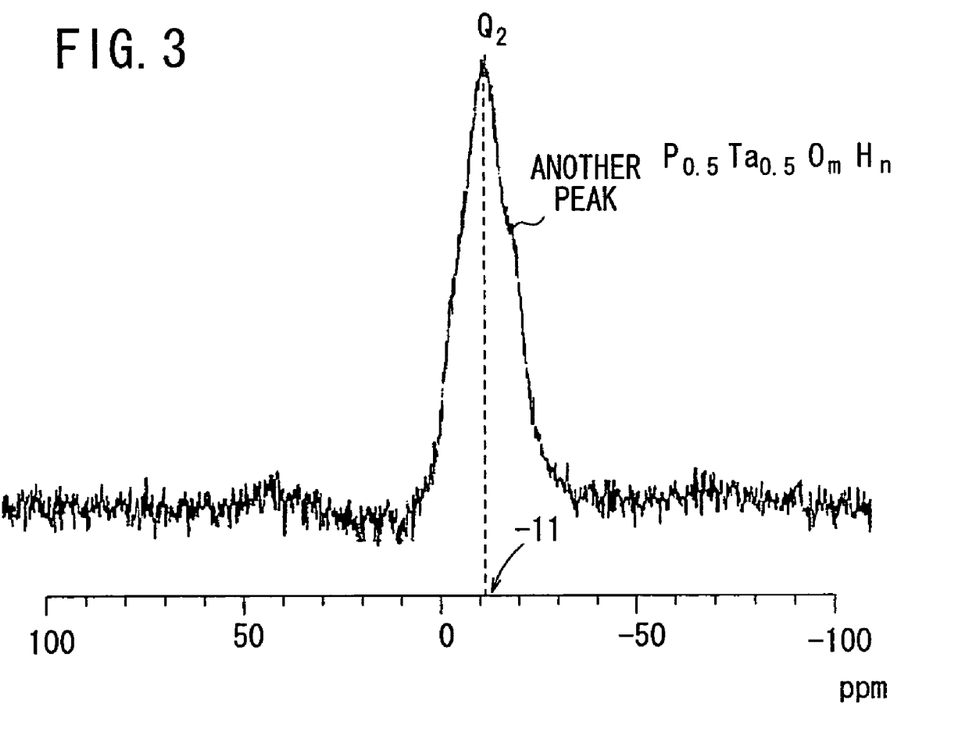
FIG. 3 is a chart of P$^{31}$-MASNMR for a P$_{0.5}$Ta$_{0.5}$O$_m$H$_n$ composite oxide glass as a proton conductor according to another embodiment.

As shown in FIG. 3, the peak $Q_0$ does not appear as well in a chart of $P^{31}$-MASNMR for a composite oxide glass of P and Ta having a composition formula represented by $P_{0.5}Ta_{0.5}O_mH_n$. In this case, there are a broad maximum peak $Q_2$ having an apex in the vicinity of −11 ppm and another peak slightly protruding from a curve near the maximum peak $Q_2$ and having an apex in the vicinity of −20 ppm. As described above, the chemical shift is the difference between the value at which the peak $Q_0$ appears resulting from orthophosphoric acid and the value at which the maximum peak $Q_2$ appears. Therefore, in this case, the chemical shift is −11 ppm.

The reason, why the chemical shift occurs toward the minus side, is as follows. When the P—OH bond in the hydroxyl group of orthophosphoric acid is substituted, for example, with the P—O—Al bond, electrons are donated from Al to P. In other words, this is caused by the so-called electron shield effect in which P is shielded when the electron cloud concentrates relatively dominantly on the P side.

Figure 4:
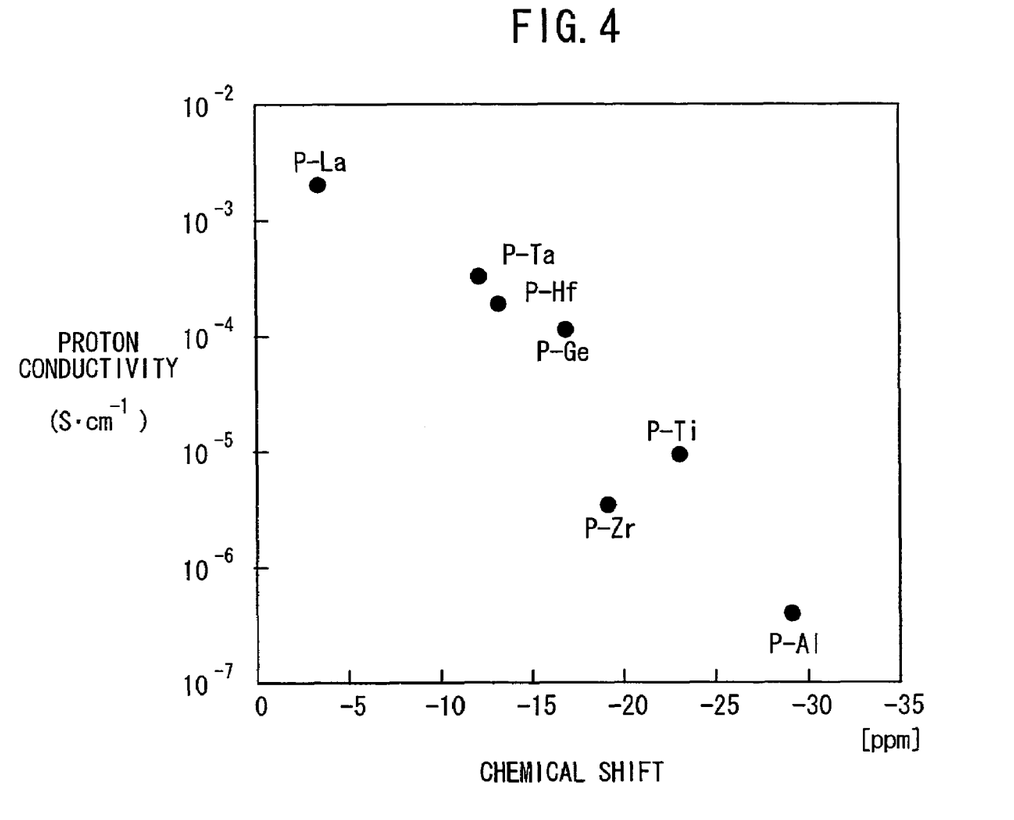
FIG. 4 is a graph illustrating a relationship between the magnitudes of the chemical shifts of respective composite oxide glasses and the proton conductivities at 80° C. in an atmosphere which assumes a fuel utilization factor of 50%.

FIG. 4 shows, as a graph, relationships between the magnitudes of the chemical shifts of respective composite oxide glasses and the proton conductivities at 80° C. in an atmosphere which assumes a fuel utilization factor of 50%. The proton conductivity was measured in accordance with the four-terminal method in which the measuring frequency was 0.1 to 1 MHz and the applied voltage was 10 to 30 mV by using an impedance analyzer produced by Solartron on condition that four Au wires were secured with paste-like Ag electrodes to a quadratic prism-shaped test piece of 4.5 mm×3 mm×15 mm to use the Au wires as lead wires. The same or equivalent procedure was also adopted in the following experiments.

As shown in FIG. 4, the smaller the chemical shift is, the larger the proton conductivity is. According to this fact, it is understood that the smaller the contribution of the electron shield effect of the metal element Me with respect to P is, the higher the proton conductivity is.

Figure 5:
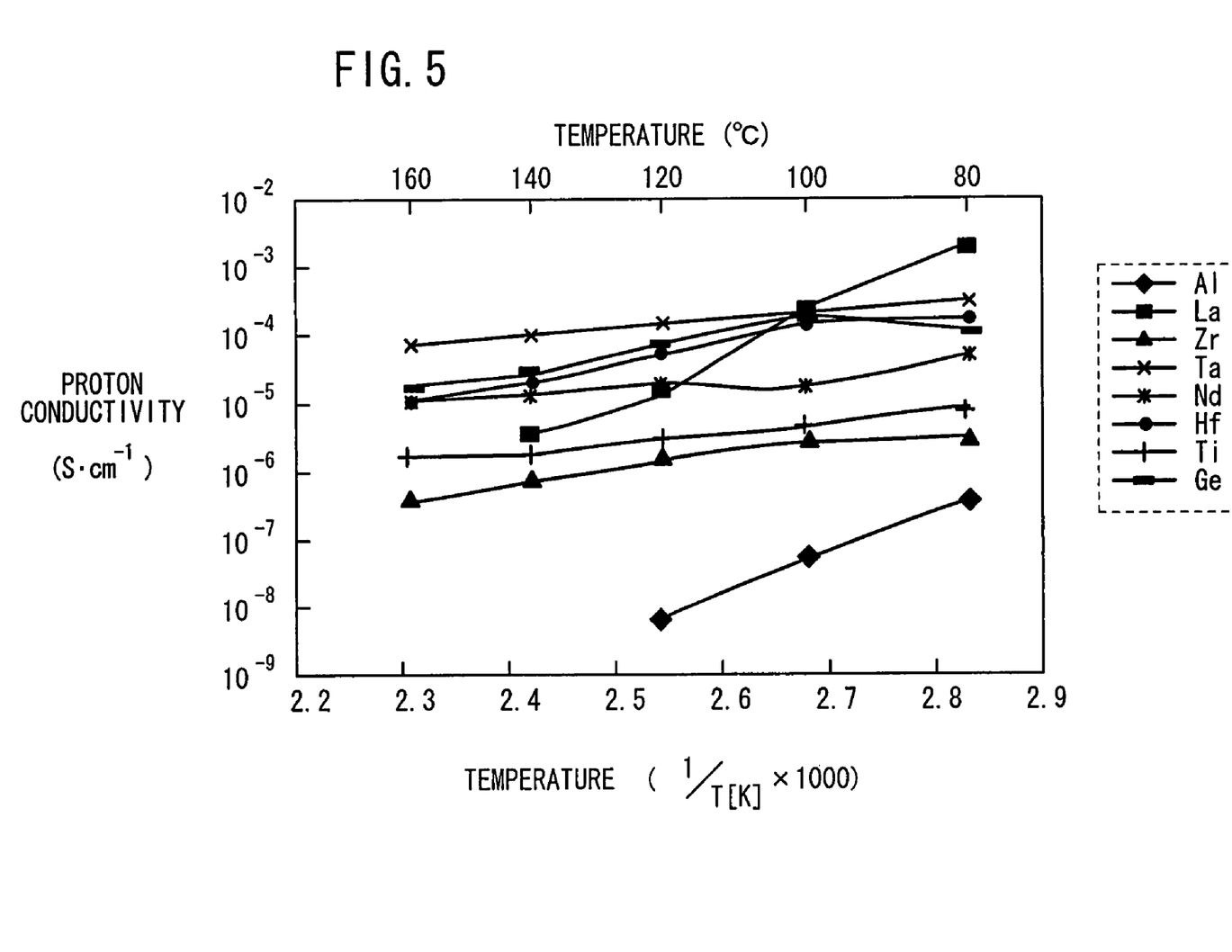
FIG. 5 is a graph illustrating, as temperature-dependent functions, proton conductivities of respective composite oxide glasses.

FIG. 5 shows, as temperature-dependent functions, proton conductivities of respective composite oxide glasses according to embodiments of the present invention each containing a constituent element of La, Ta, Hf, Ge, Nd, or Ti as the metal element in which the chemical shift as defined above is not more than −25 ppm, and proton conductivities of respective composite oxide glasses each containing a constituent element of Al (see FIG. 4) as a metal element in which the chemical shift exceeds −25 ppm. In any one of the glasses, the composition ratio between P and each of the metal elements is 1:1.

According to FIG. 5, it is understood that any sufficient proton conductivity is not obtained in the case of the composite oxide glass in which the chemical shift exceeds −25 ppm and that the excellent proton conductivity is obtained by the composite oxide glass in which the chemical shift is within −15 ppm.

The reason, why the excellent proton conductivity is obtained by the composite oxide glass in which the chemical shift is within −15 ppm, is considered to be as follows. The ion radius of the metal element contained in the composite oxide glass is larger than those of other metal elements. That is, the metal element with large ion radius has a large bonding distance with respect to P. Therefore, the electron shield effect is decreased with respect to P. Accordingly, the state of electrons in the composite oxide glass containing the metal element becomes substantially equivalent to the state of electrons in orthophosphoric acid. It is speculated that the proton conductivity is increased as compared with other metal elements for this reason.

Figure 6:
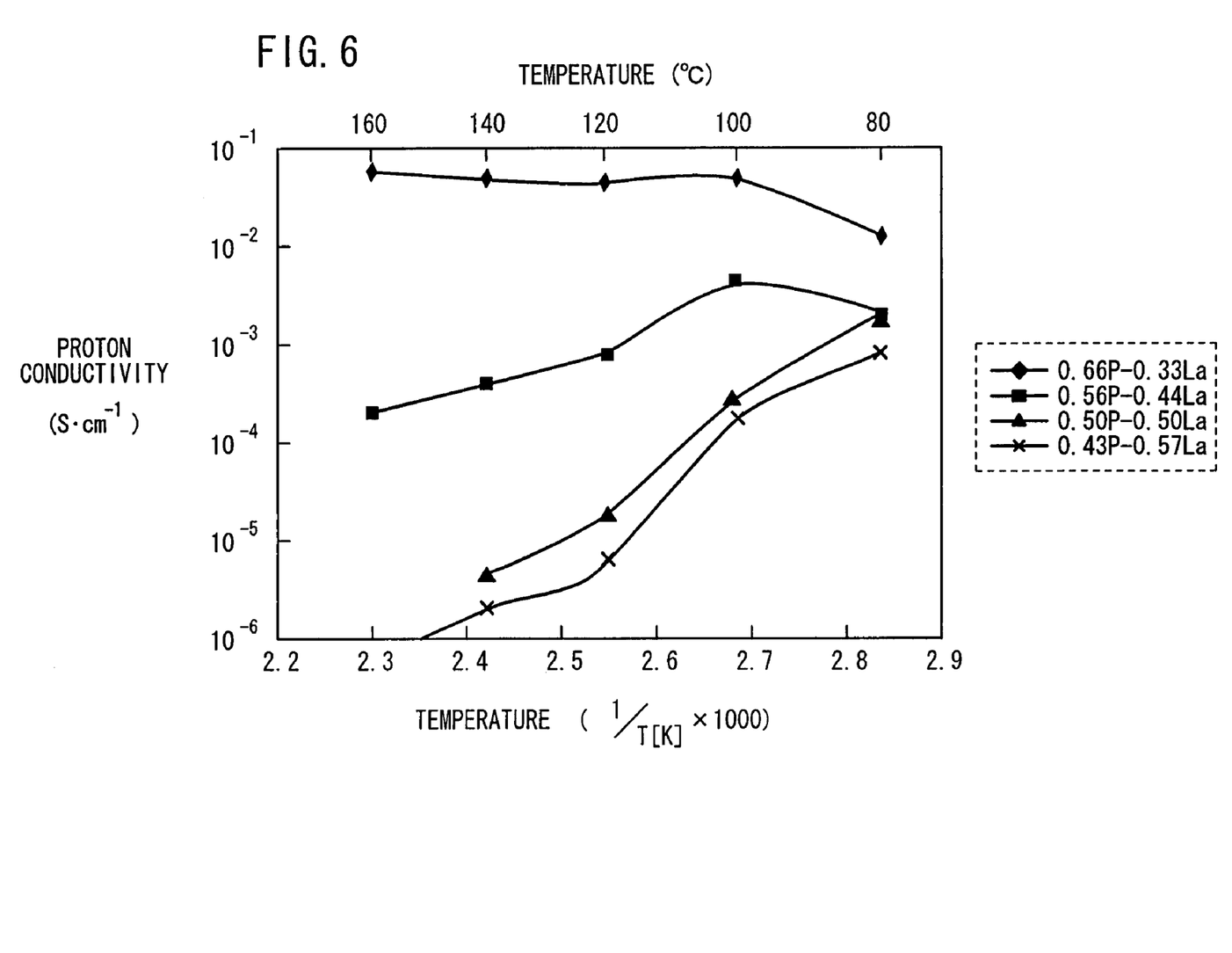
FIG. 6 is a graph illustrating, as temperature-dependent functions, proton conductivities of substances in which values of x and y are changed in P$_x$La$_y$O$_m$H$_n$ composite oxide glasses.

The proton conductivity of the composite oxide glass can be also controlled by changing the composition ratio between P and Me. For example, FIG. 6 shows, as temperature-dependent functions, proton conductivities of the $PLa_y$-$O_mH_n$ composite oxide glasses wherein x:y=0.67:0.33, 0.56: 0.44, 0.5:0.5, and 0.43:0.57. In this case, the proton conductor, in which the proton conductivity is not lowered even at 100 to 160° C., can be obtained by increasing the composition ratio of P.

It is noted that the chemical shift does not differs even when the composition ratio between P and Me differs.

Figure 7:
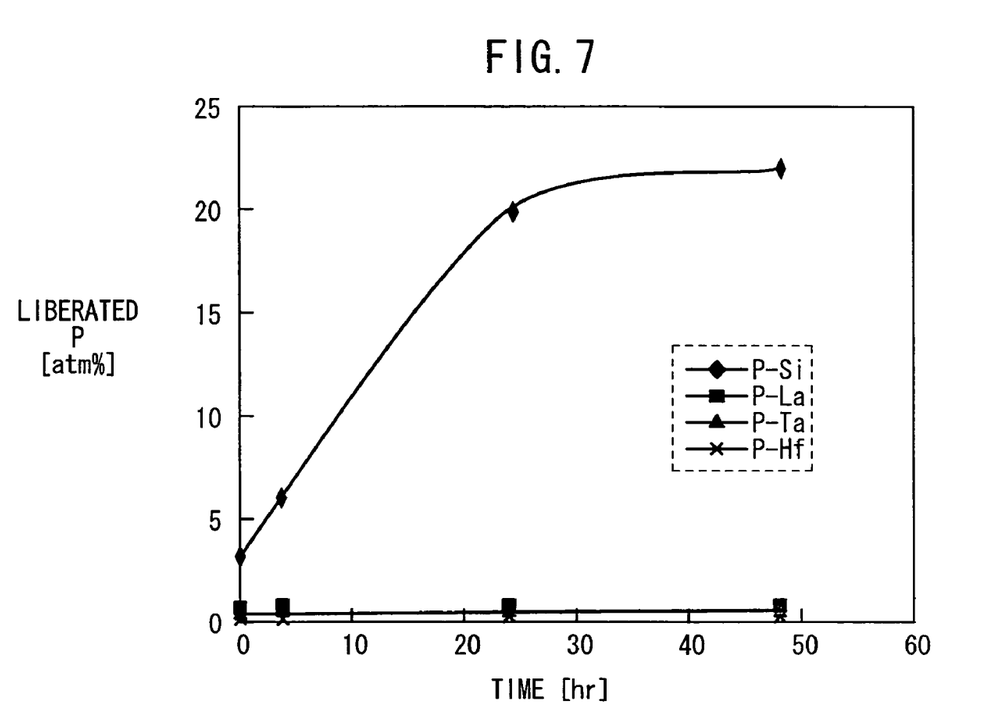
FIG. 7 is a graph illustrating the time-dependent changes of ratios of existence of liberated P in respective composite oxide glasses.

FIG. 7 shows, in combination, a graph illustrating the time-dependent changes of the ratios of existence of liberated or free P in the $P_{0.5}La_{0.5}O_mH_n$ composite oxide glass, the $P_{0.5}Ta_{0.5}O_mH_n$ composite oxide glass, the $P_{0.5}Hf_{0.5}O_mH_n$ composite oxide glass, and the $P_{0.5}Si_{0.5}O_mH_n$ composite oxide glass (silicon oxide-phosphate glass), respectively. The ratio of existence of liberated P was determined based on the peak area obtained by $P^{31}$-MASNMR, and the vertical axis of the graph indicates the atomic %.

According to FIG. 7, the following fact is clarified. That is, P is progressively liberated as the time elapses in the case of the $P_{0.5}Si_{0.5}O_mH_n$ composite oxide glass. According to the embodiments of the present invention, in contrast, liberated P is not increased, in other words, P is hardly liberated even when the time elapses in the case of the respective composite oxide glasses. This means that the hydrolysis is hardly advanced in the respective composite oxide glasses according to the embodiments of the present invention.

The proton conductor as described above can be produced, for example, as follows.

At first, a metal alkoxide, for example, lanthanum triisopropoxide ($La(O-i-C_3H_7)_3$) or tantalum pentaethoxide ($Ta(O-C_2H_5)_5$), which includes Me as the constituent element as described above, is added to a solvent such as isopropyl alcohol or ethyl alcohol, then agitated while being refluxed for about 5 hours at 50° to 80° C. in an inert atmosphere such as Ar to prepare a first solution. On the other hand, $H_2O$, $H_3PO_4$, and isopropyl alcohol are mixed with each other, then agitated for about 5 hours to prepare a second solution. As for the amounts of the metal alkoxide and $H_3PO_4$, it is appropriate that the molar ratio between Me in the first solution and P in the second solution is 1:1 when the composition ratio between Me and P is 1:1 in the composite oxide glass as the final product.

Subsequently, the second solution is dropped to the first solution which is maintained at 50° to 80° C. Accordingly, the metal alkoxide in the first solution begins to be hydrolyzed by water contained in the second solution.

After the completion of the dropping, the mixture solution is kept at about 80° C., and it is agitated while refluxed for about 10 hours. During this process, the hydrolysis of the metal alkoxide is advanced.

The hydrolyzed metal alkoxide is mutually crosslinked and condensed with $H_3PO_4$, and it is finally deposited as a solid. The solid is the composite oxide glass as represented by the structural formula described above. When the solid is separated from the solvent and it is thereafter dried by an evaporator or the like, the dry solid of the composite oxide glass is obtained.

It is preferable that a heat treatment is further applied to the dry solid so that the crosslinking is advanced. Therefore, the structure of the composite oxide glass can be further stabilized. In this procedure, it is preferable that the volume of the dry solid is previously decreased by using, for example, a planetary ball mill since the crosslinking is advanced easily and uniformly. About 1 hour is sufficient for the pulverization procedure.

It is preferable that the heat treatment is performed within a temperature range of 150° to 500° C. If the temperature is less than 150° C., the crosslinking is advanced slowly. On the other hand, if the temperature exceeds 500° C., the proton conductivity may be lowered, because the crosslinking is excessively advanced.

The period of time for the heat treatment may be controlled depending on the temperature, for example, such that the period is prolonged when the temperature is low, or the period is shortened when the temperature is high. For example, when the heat treatment temperature is 300° C., the temperature may be maintained for about 1 hour.

The composite oxide glass (proton conductor), which hardly causes the hydrolysis and which exhibits the excellent proton conductivity, is obtained as described above.

Figure 8:
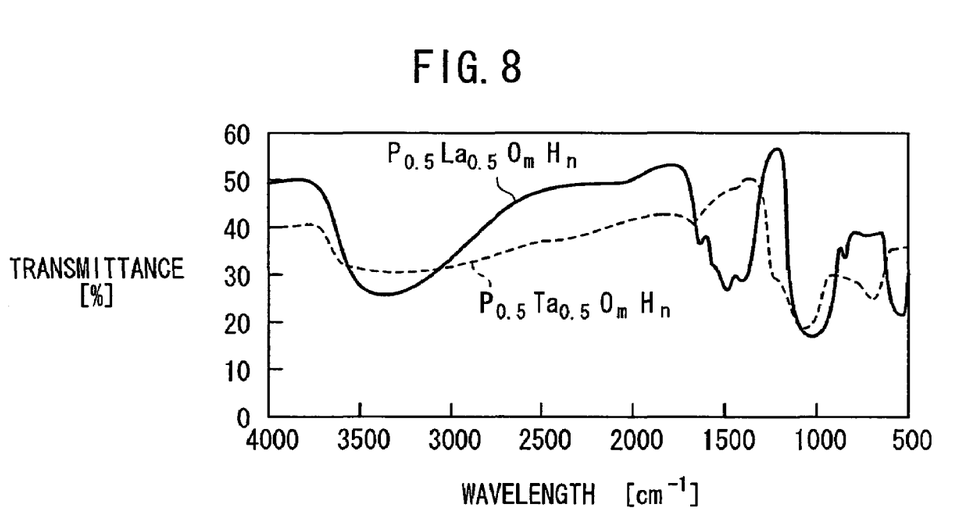
FIG. 8 is a chart illustrating results of the measurement of the P$_{0.5}$La$_{0.5}$O$_m$H$_n$ composite oxide glass and the P$_{0.5}$Ta$_{0.5}$O$_m$H$_n$ composite oxide glass by the IR method.

It is easily confirmed from the X-ray diffraction measurement that the substance obtained as described above is the amorphous composite oxide, i.e., the composite oxide glass. Further, FIG. 8 shows results of the measurement based on the infrared spectroscopy (IR) method of the $P_{0.5}La_{0.5}O_mH_n$ composite oxide glass and the $P_{0.5}Ta_{0.5}O_mH_n$ composite oxide glass. As shown in FIG. 8, the peaks based on the hydroxyl groups appear in the vicinity of the wavelength of 3400 $cm^{-1}$ in both of the glasses. According to this fact, it is understood that the hydroxyl groups exist in both of the glasses.

In order to obtain a predetermined shape of the composite oxide glass, a forming process may be performed in addition to the steps described above.

When the composition ratio between P and Me is changed in the composite oxide glass, the amounts of the metal alkoxide and $H_3PO_4$ may be changed. For example, when a $P_{0.67}La_{0.33}O_mH_n$ composite oxide glass is manufactured, $La(O-i-C_3H_7)_3$ and $H_3PO_4$ may be mixed with each other so that the molar ratio is 0.33:0.67.

The present invention has been explained in accordance with the embodiments described above by way of example. However, in view of the contents of the disclosure, it is clear for those skilled in the art that various modifications can be made within a range without deviating from the gist or essential characteristics of the present invention.

What is claimed is:

1. A proton conductor comprising a composite oxide glass of phosphorus oxide and oxide of any one metal element selected from the group consisting of lanthanoid elements, Ti, Zr, Hf, Ta, and Ge, said composite oxide glass having hydroxyl groups existing at terminals, said proton conductor exhibiting proton conductivity in accordance with dissociation and migration of H as ions from said hydroxyl groups,
    wherein said composite oxide glass is a crosslinked and condensed composite of said phosphorus oxide and said oxide of the metal element, and
    wherein said proton conductor has a chemical shift within −25 ppm, said chemical shift is a difference between a value at which a peak of orthophosphoric acid appears when a silicon oxide-phosphate glass, which is a composite oxide of phosphorus oxide and silicon oxide, each having the same number of moles, is analyzed by $P^{31}$-MASNMR and a value at which a maximum peak appears when said proton conductor is analyzed by $P^{31}$-MASNMR.

2. The proton conductor according to claim 1, wherein said lanthanoid element is La.

3. A method of producing a proton conductor composed of a composite oxide glass of phosphorus oxide and oxide of any one metal element selected from the group consisting of lanthanoid elements, Ti, Zr, Hf, Ta, and Ge, said composite oxide glass having hydroxyl groups existing at terminals, said proton conductor exhibiting proton conductivity in accordance with dissociation and migration of H as ions from said hydroxyl groups, said method comprising the step of:
    mixing phosphoric acid with a metal alkoxide containing a constituent element of said metal element to obtain a mixture,
    stirring said mixture during refluxing, and crosslinking and condensing said phosphoric acid and said metal alkoxide while hydrolyzing said metal alkoxide to obtain a solid of said composite oxide glass, which is a crosslinked and condensed composite having hydroxyl groups bonded to terminals thereof.

4. The method of producing said proton conductor according to claim 3, further comprising a step of applying a heat treatment to said solid.

5. The method of producing said proton conductor according to claim 4, wherein said solid is previously pulverized before applying said heat treatment.

* * * * *